United States Patent [19]
Katsumata et al.

[11] Patent Number: 5,017,482
[45] Date of Patent: May 21, 1991

[54] PROCESS FOR PRODUCING L-ARGININE

[75] Inventors: Ryoichi Katsumata; Haruhiko Yokoi, both of Machida, Japan

[73] Assignee: Kyowa Hakko Kogyo Co., Ltd., Tokyo, Japan

[21] Appl. No.: 99,798

[22] Filed: Sep. 22, 1987

[30] Foreign Application Priority Data

Sep. 22, 1986 [JP] Japan ................... 61-224189

[51] Int. Cl.$^5$ ............ C12P 13/10; C12N 1/21; C12N 15/52; C12N 15/74
[52] U.S. Cl. ................... 435/114; 435/69.1; 435/71.1; 435/170; 435/172.1; 435/172.3; 435/252.32; 435/320; 435/840; 435/84; 435/91; 536/27; 935/6; 935/9; 935/22; 935/29; 935/59; 935/60; 935/61; 935/66; 935/72
[58] Field of Search ........... 435/106, 320, 114, 172.3, 435/252.33, 849, 69.1, 71.1, 172.1, 172.3, 252.3, 252.32, 840, 843, 848; 536/27; 935/6, 22, 33, 60, 72

[56] References Cited
U.S. PATENT DOCUMENTS 4,775,623 10/1988 Katsumata et al. ............... 435/114

OTHER PUBLICATIONS

Cunin, 1983, In: *Amino Acids*, Hermann and Somerville (eds), Addison-Wesley Publ., Co., London, pp. 67-69.
Kharitonov et al., *Chemical Abstracts*, Vol. 105(21), Abst.#185243j; In: Mol. Genet. Mikrobiol. Virusol., 1986, vol. 8(9) pp. 29-33 (Russian).

*Primary Examiner*—Richard A. Schwartz
*Assistant Examiner*—Richard C. Peet
*Attorney, Agent, or Firm*—Antonelli, Terry, Stout & Kraus

[57] ABSTRACT

L-arginine is produced by constructing a recombinant DNA composed of a vector DNA and a DNA fragment derived from chromosomal DNA of a microorganism belonging to the genus Corynebacterium or Brevibacterium and bearing genetic information relating to the synthesis of L-arginine-biosynthetic enzyme, introducing the recombinant DNA in a microorganism belonging to the genus Corynebacterium or Brevibacterium, culturing the microorganism in a medium, and recovering L-arginine accumulated in the culture broth.

3 Claims, 1 Drawing Sheet

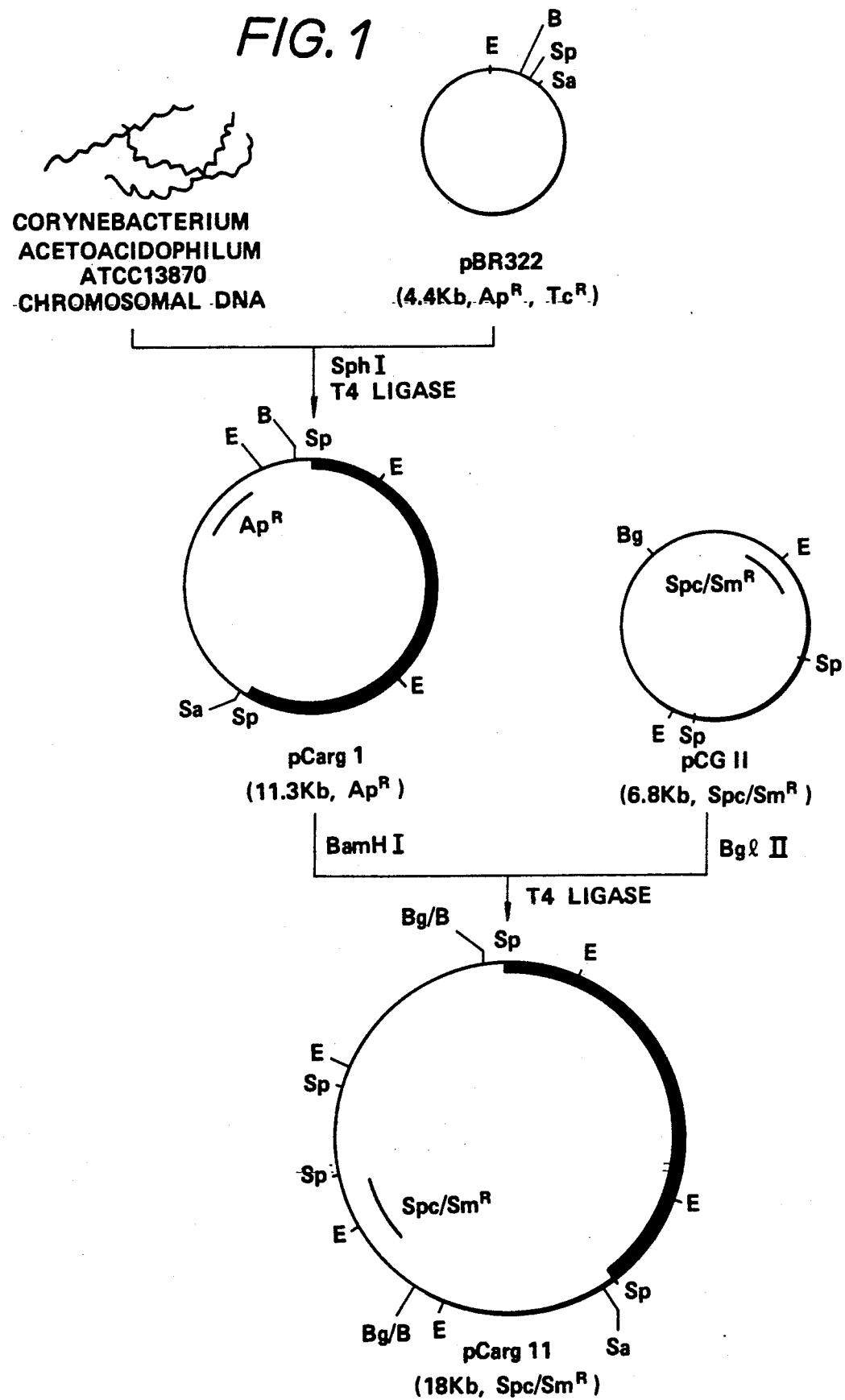

PROCESS FOR PRODUCING L-ARGININE

BACKGROUND OF THE INVENTION

As the fermentation process for producing L-arginine by using glutamic acid-producing coryneform bacteria of the genus Corynebacterium, Brevibacterium or the like, there have been known processes in which mutants derived from wild type strains of such genus are used. Examples of these L-arginine-producing mutants include strains endowed with resistance to amino acid analogues or nucleic acid analogues, which may optionally be further endowed with nucleic acid base-requirement, as described in Agric. Biol. Chem., 36, 1675–1684 (1972), Japanese Published Examined Patent Application No. 37235/79 and Japanese Published Unexamined Patent Application No. 150381/82.

Further, it is known that strains constructed by recombinant DNA technology can be used for producing L-arginine. For example, L-arginine can be produced by introducing a recombinant plasmid DNA including a DNA fragment containing a gene of an enzyme relating to the biosynthesis of arginine and derived from *Escherichia coli* in a strain of the genus Corynebacterium or Brevibacterium by and Culturing the transformant thus obtained (Japanese Published Unexamined Patent Application No. 66989/85).

With the increasing demand for L-arginine in recent years, further improvement in the process for producing this amino acid has been desired.

As a result of intensive studies to increase the L-arginine productivity of a microorganism belonging to the genus Corynebacterium or Brevibacterium by recombinant DNA technology, it was found that productivity could be increased by introducing a recombinant plasmid (pEarg1) containing a gene of *Escherichia coli* that codes for an enzyme relating to the biosynthesis of L-arginine to a strain of the genus Corynebacterium or Brevibacterium (Japanese Published Unexamined Patent Application No. 66989/85). Further studies have now revealed that strains with higher L-arginine productivity as compared with pEarg1-carrying strains can be obtained by introducing in a microorganism of the genus Corynebacterium or Brevibacterium a recombinant plasmid containing a gene that relates to the synthesis of at least one enzyme selected from the group consisting of those relating to the biosynthesis of L-arginine in a microorganism of the genus Corynebacterium or Brevibacterium, particularly, N-acetylglutamate kinase (hereinafter abbreviated to AGK), N-acetyl-γ-glutamyl-phosphate reductase (hereinafter abbreviated to AGPR), N-acetylornithine-δ-aminotransferase (hereinafter abbreviated to AOAT), ornithine carbamyltransferase (hereinafter abbreviated to OCT), an enzyme having an activity to alter N-acetylglutamate synthetase (hereinafter abbreviated to AGS)-deficient mutants of *Escherichia coli* which have arginine-requirement to non-arginine-requiring strains, and an enzyme having an activity to alter N-acetylornithine deacetylase (hereinafter abbreviated to AOD)-deficient mutants of *Escherichia coli* which have arginine-requirement to non-arginine-requiring strains. The present invention has been accomplished based on these findings.

SUMMARY OF THE INVENTION

The present invention relates to a process for producing L-arginine which comprises culturing in a culture medium a microorganism belonging to the genus Corynebacterium or Brevibacterium that carries a recombinant DNA composed of a vector DNA and a DNA fragment derived from a microorganism belonging to the genus Corynebacterium or Brevibacterium and bearing genetic information relating to the synthesis of at least one member selected from the group consisting of AGK, AGPR, AOAT, OCT, an enzyme having an activity to alter AGS-deficient mutants of *Escherichia coli* which have arginine-requirement to non-arginine-requiring strains, and an enzyme having an activity to alter AOD-deficient mutants of *Escherichia coli* which have arginine-requirement to non-arginine-requiring strains, and recovering L-arginine formed and accumulated in the culture broth. Thus, the present invention is related to the industrial field of bioindustry, and particularly to the manufacture of L-arginine which is a useful substance in the pharmaceutical and food industries.

BRIEF DESCRIPTION OF THE DRAWINGS

FIG. 1 illustrates the cleavage maps of pCarg1 and pCarg11 for restriction enzymes, SphI, EcoRI, BamHI, BglII and SalI, and the steps for constructing these plasmids, in which E, Sp, Sa, B and Bg represent the cleavage sites for EcoRI, SphI, SalI, BamHI and BglII, respectively. The sizes of plasmids are expressed in kilobase (kb). The genes coding for arginine-biosynthetic enzymes derived from the chromosomal DNA of *Corynebacterium acetoacidophilum* ATCC 13870 are included in the parts indicated by the thick solid lines of pCarg1 and pCarg11.

DETAILED DESCRIPTION OF THE INVENTION

The present invention provides a process for producing L-arginine which comprises culturing in a culture medium a microorganism belonging to the genus Corynebacterium or Brevibacterium that carries a recombinant DNA composed of a vector DNA and a DNA fragment derived from a microorganism belonging to the genus Corynebacterium or Brevibacterium and bearing genetic information relating to the synthesis of one or more L-arginine-biosynthetic enzymes; accumulating L-arginine in the culture broth; and recovering L-arginine therefrom.

The genetic information relating to the synthesis of an L-arginine-biosynthetic enzyme relates to, for example, the synthesis of at least one of AGK, AGPR, AOAT, OCT, an enzyme having an activity to alter AGS-deficient mutants of *Escherichia coli* which have arginine-requirement to non-arginine-requiring strains, and an enzyme having an activity to alter AOD-deficient mutants of *Escherichia coli* which have arginine-requirement to non-arginine-requiring strains.

Any of the strains known as glutamic acid-producing coryneform bacteria may be used as the host microorganism belonging to the genus Corynebacterium or Brevibacterium. Preferred examples are as follows.
Corynebacterium glutamicum: ATCC 13032
Corynebacterium glutamicum: ATCC 31833
Corynebacterium acetoacidophilum: ATCC 13870
Corynebacterium herculis: ATCC 13868
Corynebacterium lilium: ATCC 15990
Brevibacterium divaricatum: ATCC 14020
Brevibacterium flavum: ATCC 14067
Brevibacterium imaliophilum: ATCC 14068
Brevibacterium lactofermentum: ATCC 13869
Brevibacterium thiogenitalis: ATCC 19240

Besides wild-type strains having no ability to produce L-arginine, mutants capable of producing L-arginine, such as those resistant to amino acid analogues and other known mutants, may be used as the host microorganism.

As the donor strain of the gene encoding the enzyme relating to the biosynthesis of L-arginine, any glutamic acid-producing coryneform bacterium having the corresponding enzyme activity may be used. For example, wild-type strains of the genus Corynebacterium or Brevibacterium, and L-arginine-producing mutants derived therefrom are employed. Chromosomal DNA of these strains can be isolated, as disclosed in Japanese Published Unexamined Patent Application No. 126789/83, by treating the cells that have been treated with penicillin during culturing with lysozyme and a surface-active agent for bacteriolysis, and removing proteins by a conventional method, followed by precipitation with ethanol.

As the vector for inserting a DNA fragment obtained from the chromosomal DNA and containing the gene encoding an enzyme relating to the biosynthesis of L-arginine, any plasmid which is autonomously replicable in microorganisms belonging to the genus Corynebacterium or Brevibacterium may be used. Examples of such plasmids are pCG1 (Japanese Published Unexamined Patent Application No. 134500/82), pCG2 (Japanese Published Unexamined Patent Application No. 35197/83), pCG4 and pCG11 (Japanese Published Unexamined Patent Application No. 183799/82), pCE51, pCE52 and pCE53 [Mol. Gen. Genet., 196, 175 (1984)], and pCE54 and pCB101 (Japanese Published Unexamined Patent Application No. 105999/83). As disclosed in Japanese Published Unexamined Patent Application Nos. 134500/82 and 186489/82, plasmid vectors can be isolated and purified as ccc-DNA by treating the cells with lysozyme and a surface-active agent for bacteriolysis, preparing the cleared lyzate therefrom, precipitating DNAs with polyethylene glycol, and subjecting the DNAs thus obtained to cesium chloride/ethidium bromide density-gradient centrifugation.

The recombinant DNA composed of a vector plasmid and a DNA fragment containing the gene encoding an enzyme relating to the biosynthesis of arginine can be obtained as a mixture with various recombinant DNAs according to the ordinary procedures, by cleaving the chromosomal DNA and the vector plasmid DNA with a restriction enzyme followed by, if necessary, treatment of the cleaved ends with a terminal transferase or DNA polymerase, and ligating both DNAs by the action of a DNA ligase [Methods in Enzymology, 68 (1979)].

The mixture of ligated DNAs thus obtained is used to transform a mutant strain of the genus Corynebacterium or Brevibacterium deficient in an enzyme relating to the biosynthesis of arginine, and a transformant in which the deficiency is complemented is selected. Transformation of a strain of the genus Corynebacterium or Brevibacterium can be carried out by the method using protoplasts (Japanese Published Unexamined Patent Application Nos. 186492/82 and 186489/82, specifically described in Examples). The recombinant plasmid composed of a vector DNA and a DNA fragment containing the gene of the enzyme that relates to the biosynthesis of arginine can be obtained from the transformant by recombinant DNA techniques.

Alternatively, a host-vector system on which recombinant DNA techniques have already been established such as that of *Escherichia coli* may be used in place of the system by which the recombinant DNA is directly selected using a strain of the genus Corynebacterium or Brevibacterium as described above. That is, in vitro reaction product of the ligation of a vector DNA of *Escherichia coli* and a DNA fragment containing the said gene is used to transform a mutant of *Escherichia coli* deficient in the gene of the enzyme that relates to the biosynthesis of arginine. A transformant in which the deficiency is complemented is selected, and a cloned DNA fragment containing the said gene is obtained from the transformant. The cloned DNA fragment is recombined with the vector DNA of the genus Corynebacterium or Brevibacterium in vitro and the recombinant DNA thus obtained is used to transform a strain of the genus Corynebacterium or Brevibacterium.

Thus, a recombinant DNA containing a wild-type gene encoding an arginine-biosynthetic enzyme can be obtained by using the chromosomal DNA of a wild-type strain of the genus Corynebacterium or Brevibacterium. The recombinant DNA is introduced into a suitable strain of the genus Corynebacterium or Brevibacterium through transformation, whereby the arginine productivity of the strain can be increased.

It is known that, in glutamic acid-producing coryneform bacteria such as microorganisms of the genus Corynebacterium or Brevibacterium, the synthesis of the enzymes involved in the L-arginine synthetic pathway is repressed by arginine [Yoshida, H., et al., Agric. Biol. Chem., 43, 105 (1979)]. It is also known that, AGK, the second enzyme in the L-arginine synthetic pathway, is subject to feedback inhibition by arginine [Udaka, S., J. Bacteriol., 91, 617 (1966)]. These facts suggest that synthesis and catalytic reaction of the enzymes encoded by the wild-type genes cloned from the genus Corynebacterium or Brevibacterium would be affected by arginine. Therefore, it is preferable to use a recombinant plasmid containing a mutant gene free from control by arginine in order to further improve the arginine productivity. Such recombinant plasmids containing a mutant gene free from control by arginine can be obtained by using the chromosomal DNA of a mutant strain containing the gene of AGK insensitive to the inhibition by L-arginine, which is selected based on the resistance to L-arginine analogues (e.g., D-arginine), according to the same method as in the case of the wild-type gene as described in Agric. Biol. Chem., 43, 1899 (1979). Alternatively, these recombinant plasmids may be obtained by in vitro mutagenesis of a recombinant plasmid containing a wild-type gene according to the method shown in Mol. Gen. Genet., 145, 101 (1978), or by in vivo mutagenesis of a strain carrying a recombinant plasmid containing a wild-type gene The thus obtained recombinant plasmid containing a wild-type or mutant gene relating to the biosynthesis of arginine can be introduced into a strain of the genus Corynebacterium or Brevibacterium by the transformation method using a protoplast as mentioned above. Production of L-arginine by such a transformant carrying the recombinant plasmid can be carried out by the same method as in a conventional process for producing L-arginine by fermentation.

The transformant is cultured in an ordinary culture medium containing carbon sources, nitrogen sources, inorganic compounds, amino acids, vitamins and other nutrients under aerobic conditions while adjusting the temperature, pH, etc., and L-arginine accumulated in the culture medium is recovered therefrom.

As the carbon source, various carbohydrates such as glucose, glycerol, fructose, sucrose, maltose, mannose, starch, starch hydrolyzate and molasses; polyalcohols; and various organic acids such as pyruvic acid, fumaric acid, lactic acid and acetic acid can be used. Furthermore, hydrocarbons, alcohols, etc. can be used depending upon the assimilability of the strain employed. Particularly, blackstrap molasses is preferably used.

As the nitrogen source, ammonia; various inorganic and organic ammonium salts such as ammonium chloride, ammonium sulfate, ammonium carbonate and ammonium acetate; urea and other nitrogen-containing substances; and nitrogen-containing organic substances such as peptone, NZ-amine, meat extract, yeast extract, corn steep liquor, casein hydrolyzate, fish meal or its digested product, defatted soybean cake or its digested product and chrysalis hydrolyzate can be used.

As the inorganic compounds, dipotassium hydrogenphosphate, potassium dihydrogenphosphate, ammonium sulfate, ammonium chloride, magnesium sulfate, sodium chloride, ferrous sulfate, manganese sulfate, calcium carbonate, etc. can be used. Amino acids and vitamins need not be added if they are supplied to the medium as components of the nutrients mentioned above.

Cultivation is carried out under aerobic conditions, for example, by shaking culture or by aeration-stirring culture, preferably at a temperature in the range of 20° to 40° C. The pH of the medium is preferably maintained around neutrality during the cultivation. L-arginine is accumulated in the medium usually by culturing for one to five days.

After being cultured, the cells are removed from the culture broth, and the resulting culture liquor is treated in a known manner (e.g., treatment with activated carbon or ion-exchange resins) to recover L-arginine.

L-arginine can thus be produced in higher yields by using a strain of the genus Corynebacterium or Brevibacterium carrying a recombinant plasmid that contains the gene encoding an enzyme relating to the biosynthesis of arginine derived from glutamic acid-producing coryneform bacteria, as compared with the case where strains which do not carry such a recombinant plasmid are used.

Examples of such strains include *Corynebacterium glutamicum* K64 (FERM BP-1114) and *Corynebacterium glutamicum* K65 (FERM BP-1115), which were deposited with the Fermentation Research Institute, Agency of Industrial Science and Technology (FRI) on July 24, 1986.

A certain specific embodiment of the invention is illustrated by the following representative example.

EXAMPLE

(1) Preparation of chromosomal DNA of *Corynebacterium acetoacidophilum* ATCC 13870

Seed culture (10 ml) of *Corynebacterium acetoacidophilum* ATCC 13870 cultured in NB medium (a medium consisting of 20 g/l bouillon powder and 5 g/l yeast extract; pH 7.2) was inoculated into 400 ml of semi-synthetic medium SSM [a medium consisting of 20 g/l glucose, 10 g/l $(NH_4)_2SO_4$, 3 g/l urea, 1 g/l yeast extract, 1 g/l $KH_2PO_4$, 0.4 g/l $MgCl_2.6H_2O$, 10 mg/l $FeSO_4.7H_2O$, 0.2 mg/l $MnSO_4.4–6H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 μg/l biotin and 1 mg/l thiamine hydrochloride; pH 7.2], and was cultured with shaking at 30° C. The optical density at 660 nm (OD; hereinafter the optical density is measured at 660 nm unless otherwise specified) was determined with a Tokyo Koden colorimeter, and when the OD reached 0.2, penicillin G was added to a concentration of 0.5 unit/ml. Culturing was further continued until the OD reached 0.6.

The grown cells were collected from the culture broth and washed with TES buffer solution [0.03M Tris(hydroxymethyl)aminomethane (hereinafter referred to as Tris), 0.005M disodium ethylenediaminetetraacetate (hereinafter referred to as EDTA) and 0.05M NaCl; pH 8.0]. The washed cells were suspended in 10 ml of a lysozyme solution (25% sucrose, 0.1M NaCl, 0.05M Tris and 0.8 mg/ml lysozyme; pH 8.0), and subjected to reaction at 37° C. for four hours. High molecular chromosomal DNA was isolated from the collected cells according to the method of Saito, et al. [Biochem. Biophys. Acta, 72, 619 (1963)].

(2) Preparation of restriction-deficient and arginine-requiring mutants of *Escherichia coli*

In order to facilitate the cloning of the gene of the enzyme relating to the biosynthesis of arginine derived from glutamic acid-producing coryneform bacteria which is a foreign gene in the *Escherichia coli* host-vector system, restriction-deficient and arginine-requiring mutants of *Escherichia coli* were obtained as described below to be used as host cells.

*Escherichia coli* K12 WA802 carrying host-specific restriction-deficient mutation (methionine-requiring; FERM BP-718) was mutated by using 400 γ/ml N-methyl-N'-nitro-N-nitrosoguanidine (NTG) according to a conventional method [Experiment in Molecular Genetics, P. 125, Coldspring Harbor Laboratory (1972)], and arginine-requiring strains were selected according to the concentration method for an auxotroph using penicillin [Experiment in Molecular Genetics, P. 230, Coldspring Harbor Laboratory (1972)]. The mutant genes of these arginine-requiring strains were identified by measuring the activity of each enzyme relating to the biosynthesis of arginine according to the method described in Eur. J. Biochem., 31, 290 (1972) for AGS, and to the method described in J. Gen. Microbiol., 69, 365 (1971) for AGK and AOD. As a result, EA-1 was obtained as an AGS-deficient mutant strain, EA-21 as an AGK-deficient mutant strain, and EA-4 as an AOD-deficient mutant strain.

Cloning of a DNA fragment containing the gene relating to arginine biosynthesis Cloning was carried out by using a host-vector system of *Escherichia coli* pBR322 (resistant to ampicillin and tetracyline) commercially available from Takara Shuzo Co., Ltd. was used as the vector. 10 units of restriction enzyme SphI (product of Boehringer Mannheim GmbH) was added to 200 μl of a reaction solution for SphI (6 mM Tris, 125 mM NaCl, 6 mM $MgCl_2$, 6 mM β-mercaptoethanol and 0.01% Triton X-100; pH 7.5) containing 1 μg of pBR322 plasmid DNA and 3 μg of the chromosomal DNA of *Corynebacterium acetoacidophilum* ATCC 13870 prepared in (1) above, and the mixture was subjected to reaction at 37° C. for 60 minutes, and then heated at 65° C. for 30 minutes to stop the reaction. To the resulting reaction mixture, were added 40 μl of T4 ligase buffer solution at a 10-fold concentration (660 mM Tris, 66 mM $MgCl_2$ and 100 mM dithiothreitol; pH 7.6), 4 μl of 100 mM ATP, 160 μl of water and 300 units of T4 ligase (product of Takara Shuzo Co., Ltd.), and the mixture was subjected to reaction at 12° C. for 16 hours. The reaction mixture was used for transformation of *Escherichia coli* EA-21 (arginine- and methionine-requiring) prepared in (2) above. Competent cells of EA-21 strain were prepared according to the method of Dagert, et al. [Gene., 6 23 (1979)].

That is, EA-21 strain was inoculated in 50 ml of L medium (10 g/l Bacto-Tryptone, 5 g/l yeast extract, 1 g/l glucose and 5 g/l NaCl; pH 7.2) and cultured at 37° C. until the OD reached 0.5. The culture broth was cooled on ice for ten minutes, and then subjected to centrifugation. The cells collected by centrifugation were suspended in 20 ml of cooled 0.1M $CaCl_2$ solution, and the suspension was allowed to stand at 0° C. for 20 minutes. The cells were again collected by centrifugation and resuspended in 0.5 ml of 0.1M $CaCl_2$, and the suspension was allowed to stand at 0° C. for 18 hours. To 150 μl of this $CaCl_2$-treated cell suspension was added 50 μl of the ligase reaction mixture obtained above, and the resulting mixture was allowed to stand at 0° C. for ten minutes and then heated at 37° C. for five minutes. 2 ml of L medium was added thereto, and shaking culture was carried out at 37° C. for two hours. The resulting culture was washed twice with physiological saline solution by centrifugation, and the cells were spread on the Davis' minimal agar plate medium [2 g/l glucose, 1 g/l $(NH_4)_2SO_4$, 7 g/l $K_2HPO_4$, 2 g/l $KH_2PO_4$, 0.1 g/l $MgSO_4.7H_2O$, 0.5 g/l trisodium citrate, 4 mg/l thiamine hydrochloride and 16 g/l agar; pH 7.2] containing 30 μg/ml methionine and 50 μg/ml ampicillin, and cultured at 30° C. for four days. Plasmid DNAs were isolated from the cultured cells of the transformants thus grown by the method of Ann, et al. [J. Bacteriol., 140, 400 (1979)].

Analysis by digestion with various restriction enzymes, followed by agarose gel electrophoresis, revealed that a plasmid obtained from one of the transformants and named pCarg1 had a structure wherein an SphI DNA fragment of 7 kb was inserted at the single SphI cleavage site of pBR322.

It was confirmed that a mutant obtained by transforming EA-21 strain with pCarg1 in the same manner as above and selecting based on ampicillin resistance had no arginine-requirement and that the plasmid isolated therefrom had the same structure as that of pCarg1. This indicates that the gene of *Corynebacterium acetoacidophilum* ATCC 13870 that relates to the synthesis of an enzyme having an activity to alter AGK-deficient mutants of *Escherichia coli* which have arginine-requirement to non-arginine-requiring strains has been cloned on pCarg1.

It was also confirmed that mutants obtained by transforming AGS-deficient mutant strain EA-1 and AOD-deficient mutant strain EA-4 (both are arginine- and methionine-requiring) derived from *Escherichia coli* K12 strain and prepared in (2) above with pCarg1 in the same manner as above and selecting based on ampicillin resistance had no arginine-requirement. This indicates that pCarg1 also contains the genes coding for enzymes having activities to alter AGS-deficient mutants and AOD-deficient mutants of *Escherichia coli* which have arginine-requirement to non-arginine-requiring strains.

WA802 strain which carries pCarg1 and WA802 strain which does not carry pCarg1 were examined for AGK activity, AGPR activity, AOAT activity and OCT activity according to the method of Baumberg, et al. [J. Gen. Microbiol., 69, 365 (1971)], the method of Vogel, et al. [Methods in Enzymology, 17 (Part A), 255 (1970)], the method of Vogel, et al. [Methods in Enzymology, 17 (Part A), 260 (1970)] and the method of Prescott, et al. [Anal. Biochem., 32, 408 (1969)], respectively. WA802 strain carrying pCarg1 exhibited more than three times higher activity for each enzyme activity, which indicates that pCarg1 contains the genes coding for AGK, AGPR, AOAT and OCT.

It is clear from the results obtained above that pCarg1 carries the genes derived from *Corynebacterium acetoacidophilum* ATCC 13870 and coding for AGK, AGPR, AOAT, OCT and enzymes having activities to alter AGS-deficient mutants and AOD-deficient mutants of *Escherichia coli* which have arginine-requirement to non-arginine-requiring strains.

(4) Preparation of plasmid pCarg11

A shuttle vector pCarg11 capable of replicating in both *Escherichia coli* and glutamic acid-producing coryneform bacteria was prepared by recombination of pCarg1 obtained above with vector plasmid pCG11 which is replicable in glutamic acid-producing coryneform bacteria.

pCH11 is a plasmid vector replicable in microorganisms of the genera Corynebacterium and Brevibacterium, which carries a streptomycin-spectinomycin resistance gene. pCarg11 was constructed by the process described below.

pCH11 was isolated from *Corynebacterium glutamicum* ATCC 31833 carrying pCG11 according to the method disclosed in Japanese Published Unexamined Patent Application No. 134500/82. To 100 μl of a reaction solution for restriction enzyme BglII (10 mM Tris, 100 mM NaCl and 10 mM $MgCl_2$; pH 7.5) containing 2 μg of pCG11 DNA, was added 6 units of BglII (product of Takara Shuzo Co., Ltd.), and the mixture was subjected to reaction at 37° C. for two hours, and then heated at 65° C. for 30 minutes to stop the reaction. Separately, 6 units of restriction enzyme BamHI (product of Takara Shuzo Co., Ltd.) was added to 100 μl of a reaction solution for BamHI (10 mM Tris, 100 mM NaCl and 10 mM $MgCl_2$; pH 7.5) containing 2 μg of pCarg1 DNA, and the mixture was subjected to reaction at 37° C. for two hours, and then heated at 65° C. for 30 minutes to stop the reaction. Both digestion reaction mixtures were mixed together, and 40 μl of T4 ligase buffer solution at a 10-fold concentration, 4 μl of 100 mM ATP, 150 μl of water and 300 units of T4 ligase (product of Takara Shuzo Co., Ltd.) were added thereto. The mixture was subjected to reaction at 12° C. for 16 hours. Transformation of *Escherichia coli* EA-21 was carried out in the same manner as in (3) above using this ligase reaction mixture, and the transformants thus formed were spread on the Davis' minimal agar plate medium containing 30 μg/ml methionine and 100 μg/ml spectinomycin. Plasmid DNA was isolated from a spectinomycin-resistant and non-arginine-requiring transformant grown on this plate medium according to the method of Ann, et al. [J. Bacteriol., 140, 400 (1979)]. Analysis by digestion with various restriction enzymes, followed by agarose gel electrophoresis, revealed that this plasmid had a structure in which pCG11 and pCarg1 were ligated at the single BglII cleavage site of the former and the single BamHI cleavage site of the latter (refer to FIG. 1). This plasmid was named pCarg11.

EA-1, EA-21 and EA-4 strains obtained above, all of which were derived from *Escherichia coli* K12, were transformed by using pCarg11. It was found that the obtained transformants having resistance to spectinomycin also had non-arginine-requirement.

Strains which carry pCarg11 and those which do not carry pCarg11 were examined for AGK, AGPR, AOAT and OCT activities according to the same methods as in (3) above. The strains carrying pCarg11 exhibited more than three times higher activity for each enzyme activity. These facts indicate that pCarg11 also contains the genes coding for AGK, AGPR, AOAT, OCT and the enzymes having activities to alter AGS-deficient mutants and AOD-deficient mutants of *Escherichia coli* which have arginine-requirement to non-arginine-requiring strains.

pCarg11 was then used for transforming *Corynebacterium glutamicum* ATCC 31833 according to the methods described in Japanese Published Unexamined Patent Application Nos. 186492/82 and 186489/82. The cells of ATCC 31833 strain were cultured in NB medium, and 0.4 ml of the obtained seed culture was inoculated in 40 ml of SSM medium, and subjected to shaking culture at 30° C. When the OD reached 0.15, penicillin G was added to a final concentration of 0.5 unit/ml. Culturing was further continued, and the grown cells were collected when the OD reached about 0.6. The collected cells were suspended in 5 ml of RCGP medium [5 g/l glucose, 5 g/l Casamino acid, 2.5 g/l yeast extract, 3.5 g/l $K_2HPO_4$, 1.5 g/l $KH_2PO_4$, 0.41 g/l $MgCl_2.6H_2O$, 10 mg/l $FeSO_4.7H_2O$, 2 mg/l $MnSO_4.4-6H_2O$, 0.9 mg/l $ZnSO_4.7H_2O$, 0.04 mg/l $(NH_4)_6Mo_7O_{24}.4H_2O$, 30 µg/l biotin, 2 mg/l thiamine hydrochloride, 135 g/l disodium succinate and 30 g/l polyvinylpyrrolidone (M.W.: 10,000); pH 7.6] containing 1 mg/ml lysozyme to make up about $10^9$ cells per milliliter, and the suspension was transferred into an L-tube and subjected to gentle shaking culture at 30° C. for 15 hours to make protoplasts. The protoplast suspension (0.5 ml) was taken in a small test tube and centrifuged for five minutes at 2,500×g to separate the protoplasts. The protoplasts were then suspended in 1 ml of TSMC buffer solution (10 mM $MgCl_2$, 30 mM $CaCl_2$, 50 mM Tris and 400 mM sucrose; pH 7.5) and washed by centrifugation, and the washed cells were resuspended in 0.1 ml of TSMC buffer solution. 100 µl of a 1:1 mixture of TSMC buffer solution at a two-fold concentration and pCarg11 plasmid DNA solution was added to the suspension, and 1.0 ml of TSMC buffer solution containing 20% polyethyleneglycol (PEG) 6000 (product of Nakarai Chemicals, Ltd.) was further added thereto. After three minutes, the resulting mixture was centrifuged for five minutes at 2,500×g to remove the supernatant. The precipitated protoplasts were suspended in 1 ml of RCGP medium (pH 7.4), and the suspension was subjected to gentle shaking at 30° C. for two hours. This protoplast suspension (0.3 ml) was spread on RCGP agar medium (RCGP medium containing 1.6% agar; pH 7.4) containing 400 µg/ml spectinomycin, and cultured at 30° C. for eight days.

The spectinomycin-resistant transformant thus grown was subjected to shaking culture in 400 ml of SSM medium. Penicillin G was added to a final concentration of 0.5 unit/ml when the OD reached 0.15, and shaking culture was continued until the OD reached 0.65. Then, the cells collected from the culture broth were washed with TES buffer solution, suspended in 10 ml of a lysozyme solution, and subjected to reaction at 37° C. for four hours. To the reaction mixture, were successively added 2.4 ml of 5M NaCl, 0.6 ml of 0.5M EDTA (pH 8.0) and 4.4 ml of solution comprising 4% sodium lauryl sulfate and 0.7M NaCl, and the resulting mixture was gently stirred and placed on ice for 15 hours. The whole lysate was transferred into a centrifuge tube, and subjected to centrifugation at 69,400×g at 4° C. for 60 minutes to recover the supernatant. PEG6000 (product of Nakarai Chemicals, Ltd.) in an amount corresponding to 10% by weight was added to the supernatant, and the mixture was gently stirred and then placed on ice. After ten hours, pellets were recovered by centrifugation at 1,500×g for 10 minutes and gently redissolved in 5 ml of TES buffer solution. 2.0 ml of 1.5 mg/ml ethidium bromide solution was added thereto, and cesium chloride was further added and gently dissolved to adjust the density of the solution to 1.580. The solution thus obtained was subjected to ultracentrifugation at 105,000×g at 18° C. for 48 hours, and a closed circular DNA was detected as a band at a high density level at the lower position of the centrifuge tube under UV irradiation. This band was recovered from the side of the centrifuge tube by means of a syringe, whereby plasmid was isolated. The obtained fraction was treated five times with an equal volume of an isopropyl alcohol solution (9:1 mixture of isopropyl alcohol and TES buffer solution by volume further containing a saturated amount of cesium chloride) to remove ethidium bromide by extraction, and the treated solution was then dialyzed against TES buffer solution to obtain a plasmid DNA.

Analysis by digestion with various restriction enzymes, followed by agarose gel electrophoresis, revealed that this plasmid had the same structure as pCarg11 characterized by the cleavage pattern with restriction enzymes.

Expression of the genes contained in pCarg11 in microorganisms of the genus Corynebacterium was confirmed with respect to AGK and AOAT genes by the following method.

In order to compare the degree of expression of AGK and AOAT genes in *Corynebacterium glutamicum* ATCC 31833 strain which carries pCarg11 and ATCC 31833 strain which does not carry pCarg11, crude enzyme extracts were prepared from both strains as explained below. That is, seed culture (10 ml for each strain) was inoculated into 300 ml of SSM medium (100 µg/ml spectinomycin was added only to the medium for the strain carrying pCarg11) and subjected to shaking culture at 30° C. until the OD reached about 3. The cells collected from the culture broth were washed with buffer solution A (10 mM Tris and 1 mM dithiothreitol; pH 7.2) and suspended in 10 ml of buffer solution A. The suspension was subjected to ultrasonic treatment for 20 minutes on Sonicator (TOMY Seiko Co., Ltd.; Intensity Range: 7) to disrupt the cells in the suspension, and the disrupted cell suspension was centrifuged at 16,000 rpm for 40 minutes (RPR 20-2 rotor; Hitachi, Ltd.). The supernatant was recovered and dialyzed twice against 1 liter of buffer solution A at 4° C. for six hours to remove low molecular substances.

The crude enzyme extracts thus obtained were examined for AGK activity according to the method of Baumberg, et al. [J. Gen. Microbiol., 69, 365 (1971)] and for AOAT activity according to the method of Vogel, et al. [Methods in Enzymology, 17 (Part A), 260 (1970)]. The enzyme extract obtained from ATCC 31833 strain carrying pCarg11 exhibited 30 times higher activity for AGK and 10 times higher activity for AOAT as compared with the enzyme extract obtained from ATCC 31833 strain which does not carry pCarg11. This fact indicates that the genes in pCarg11 can be expressed in glutamic acid-producing coryneform bacteria.

The pCarg11-carrying transformant thus obtained has been deposited with FRI as *Corynebacterium glutamicum* K64 (FERM BP-1114).

(5) Preparation of a mutant plasmid capable of increasing the arginine productivity of a host microorganism A mutant plasmid which is capable of increasing the L-arginine productivity of a host microorganism was prepared by direct treatment of pCarg11 DNA with hydroxylamine [Mol. Gen. Genet., 145, 101 (1978)] as described below.

pCarg11 was isolated from *Corynebacterium glutamicum* K64 (FERM BP-1114) according to the method described in (4) above. pCarg11 (2 μg) was added to 300 μl of a mutating solution (50 mM $NaH_2PO_4$, 400 mM hydroxylamine hydrochloride and 0.5 mM EDTA; pH 6.0), and the mixture was subjected to reaction at 75° C. for 60 minutes and dialyzed against TES buffer solution. The dialyzate thus obtained (100 μl) was used to transform *Corynebacterium glutamicum* ATCC 31833 in the same manner as in (4) above, and the obtained spectinomycin-resistant strains were tested for arginine productivity in the following manner. A seed culture (0.5 ml) obtained by culturing in NB medium at 30° C. for 24 hours was inoculated into 5 ml of a production medium [80 g/l blackstrap molasses (converted to glucose), 40 g/l $(NH_4)_2SO_4$, 0.5 g/l $K_2HPO_4$, 0.5 g/l $KH_2PO_4$ and 20 g/l $CaCO_3$; pH 7.0] in a test tube, and shaking culture was carried out at 30° C. for 72 hours. After culturing, the culture filtrate was subjected to paper chromatography and the amount of L-arginine produced was determined by colorimetry using ninhydrin color development. Strains which markedly surpass *Corynebacterium glutamicum* ATCC 31833 strain carrying pCarg11 in L-arginine productivity were selected. Plasmid DNAs were isolated from these strains in the same manner as in (4) above, which were subjected to structural analysis by digestion with various restriction enzymes, followed by agarose gel electrophoresis. It was found that these plasmids had the same restriction enzyme cleavage map as that of pCarg11. Of these, the plasmid isolated from the strain with the highest L-arginine productivity was named pCarg110. The strain carrying pCarg110 has been deposited with FRI as Corynebacterium glutamicum K65 (FERM BP-1115).

FIG. 1 illustrates the steps for constructing pCarg1 and pCarg11. Table 1 shows the results of L-arginine productivity test on the strains carrying pCarg11 or pCarg110, and the strain carrying pEarg1 (Japanese Published Unexamined Patent Application No. 66989/85) prepared in a way similar to that described in (4) above.

TABLE 1

| Strain | Amount of L-arginine produced (g/l) |
|---|---|
| *Corynebacterium glutamicum* ATCC 31833 | 0 |
| *Corynebacterium glutamicum* ATCC 31833/pCarg11 (K64 FERM BP-1114) | 0.1 |
| *Corynebacterium glutamicum* ATCC 31833/pCarg110 (K65 FERM BP-1115) | 3.2 |
| *Corynebacterium glutamicum* ATCC 31833/pEarg1 | 1.6 |

(6) Production of L-arginine by the strains carrying pCarg11 or pCarg110

*Corynebacterium herculis* ATCC 13868 and *Brevibacterium flavum* ATCC 14067 were transformed by using pCarg11 and pCarg110 in the same manner as in (4) above. Plasmids were isolated from the obtained spectinomycin-resistant transformants in the same manner as in (4), and their structures were analyzed by digestion with various restriction enzymes, followed by agarose gel electrophoresis. It was confirmed that these transformants carried pCarg11 or pCarg110.

L-arginine production test was conducted in the same manner as in (5) using the strains carrying pCarg11, pCarg110 or pEarg1 (Japanese Published Unexamined Patent Application No. 66989/85) and those which do not carry any one of these plasmids. The results are shown in Table 2.

TABLE 2

| Strain | Amount of L-arginine produced (g/l) |
|---|---|
| *Corynebacterium herculis* ATCC 13868 | 0 |
| *Corynebacterium herculis* ATCC 13868/pCarg11 | 0.2 |
| *Corynebacterium herculis* ATCC 13868/pCarg110 | 2.5 |
| *Corynebacterium herculis* ATCC 13868/pEarg1 | 1.8 |
| *Brevibacterium flavum* ATCC 14067 | 0 |
| *Brevibacterium flavum* ATCC 14067/pCarg11 | 0.1 |
| *Brevibacterium flavum* ATCC 14067/pCarg110 | 2.0 |
| *Brevibacterium flavum* ATCC 14067/pEarg1 | 1.0 |

What is claimed is:

1. A process for producing L-arginine which comprises culturing in a culture medium a microorganism belonging to the species *Corynebacterium glutamicum*, *Corynebacterium herculis* or *Brevibacterium flavum* that carries the recombinant DNA pCarg110; accumulating L-arginine in the culture broth; and recovering L-arginine therefrom.

2. The recombinant DNA pCarg110.

3. A microorganism belonging to the species *Corynebacterium glutamicum*, *Corynebacterium herculis* or *Brevibacterium flavum* that carries the recombinant DNA pCarg110.

* * * * *